United States Patent

Gaignoux et al.

[11] 4,092,111
[45] May 30, 1978

[54] APPARATUS FOR THE HEAT TREATMENT OF PRODUCTS CONTAINED IN SEALED CONTAINERS

[75] Inventors: Daniel Clement Gaignoux, Saint Maurice; Jean-Pierre Pinot, Boulogne sur Seine, both of France

[73] Assignees: F. Hanau S. A.; Barriquand, both of Paris, France

[21] Appl. No.: 778,456

[22] Filed: Mar. 17, 1977

Related U.S. Application Data

[63] Continuation of Ser. No. 624,567, Oct. 21, 1975, abandoned.

[30] Foreign Application Priority Data

Oct. 24, 1974   France .................................. 74 35637

[51] Int. Cl.² .......................... A23L 1/00; A23L 3/10; A61L 3/00; A61L 3/02
[52] U.S. Cl. .......................................... 21/93; 21/78; 21/105; 99/359
[58] Field of Search .................... 21/2, 78, 93, 99, 103, 21/105, 78, 80, 91, 92; 99/359; 126/346, 373, 377, 378; 165/61; 62/64, 376; 426/403, 407, 412, 521, 522

[56] References Cited

U.S. PATENT DOCUMENTS

| | | | |
|---|---|---|---|
| 866,870 | 9/1907 | Loew | 99/359 |
| 1,186,944 | 6/1916 | Rice | 99/359 |
| 1,732,321 | 10/1929 | White | 21/93 |
| 1,881,855 | 10/1932 | Mullen | 426/407 |
| 3,511,169 | 5/1970 | Fritzberg et al. | 21/93 |

FOREIGN PATENT DOCUMENTS

| | | | |
|---|---|---|---|
| 844,443 | 7/1939 | France | 99/359 |
| 378,370 | 7/1923 | Germany | 99/359 |

*Primary Examiner*—Morris O. Wolk
*Assistant Examiner*—Bradley Garris
*Attorney, Agent, or Firm*—Browdy and Neimark

[57] ABSTRACT

Heat exchange between a fluid and products in sealed containers is effected by the homogeneous repartition at an adjustable flow rate of a liquid in the course of the successive phases of the heat exchange cycle, by streaming at all points of a large and compact batch of the containers along the walls of each of the containers. The fluid circulates continuously over the containers, in the course of successive phases of the heat treatment, after the temperature of said fluid has been readjusted, within a same heat treatment operation, or regulated from one heat treatment operation to the following one. The pressure, or the vacuum, if necessary for the heat treatment, is regulated independently of the temperature. The apparatus for performing this method has a fluid distributing device comprising at least one perforated plate and a number of perforated divider plates.

11 Claims, 12 Drawing Figures

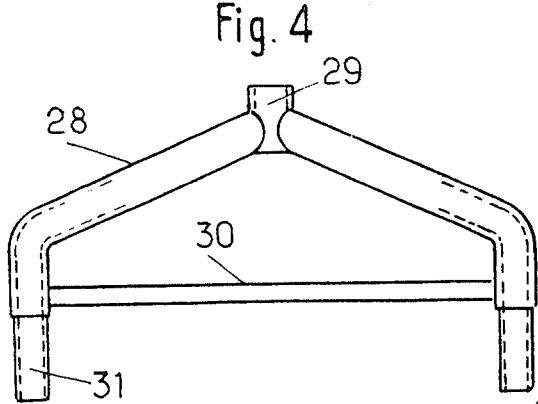
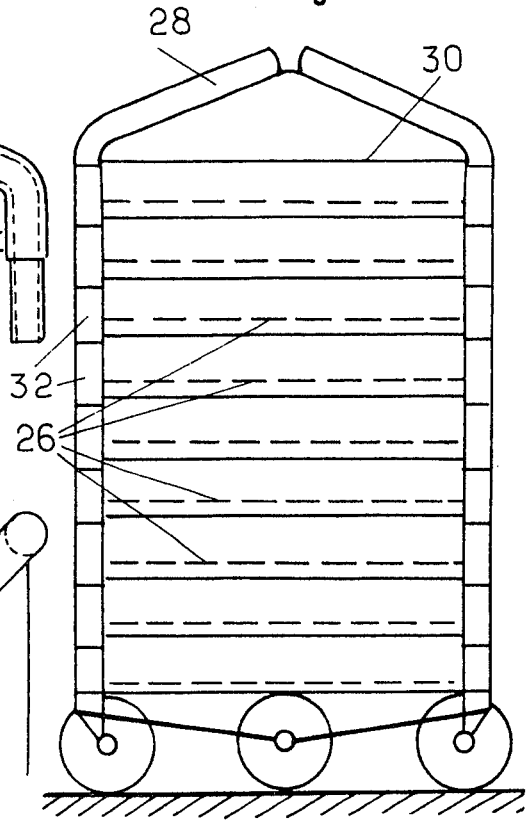
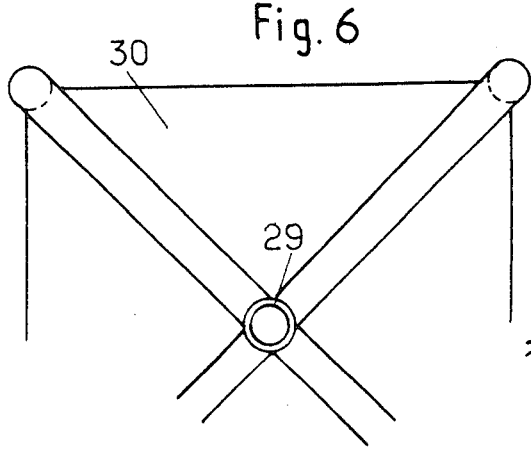
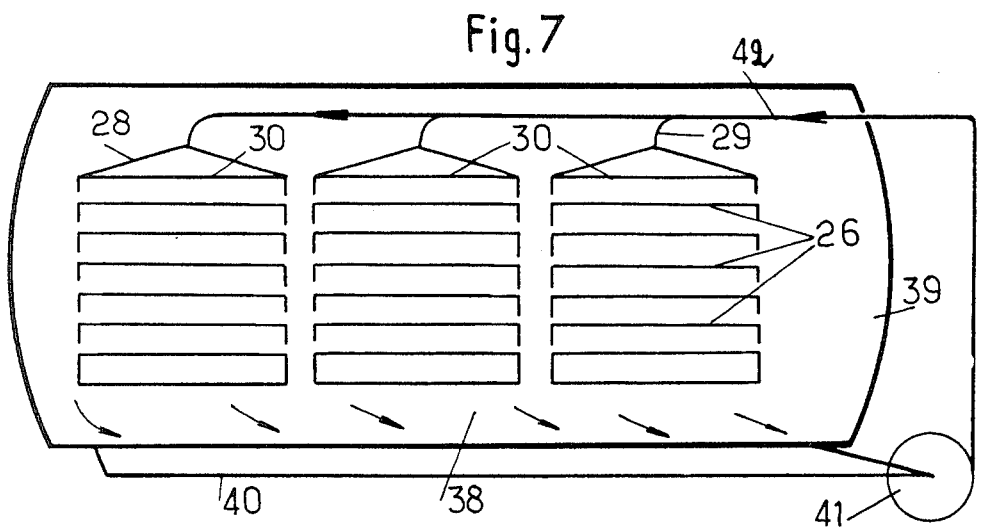

APPARATUS FOR THE HEAT TREATMENT OF PRODUCTS CONTAINED IN SEALED CONTAINERS

This is a continuation, of application Ser. No. 624,567, filed Oct. 21, 1975 and now abandoned.

BACKGROUND OF THE INVENTION

1. Field of the Invention

The present invention relates to a method for the heat treatment of products contained in sealed containers, by exchange between a fluid and said products, in particular to effect the sterilization, with or without back-pressure or excess pressure, of food, pharmaceutical or the like products in the most diverse of sealed wrappings, such as metal cans, sachets, boats, cups, of aluminum or of plastics material, or even of composite materials comprising these different elements, or also such as glass containers, etc., hereinafter sometimes referred to as sealed packages.

The present invention also relates to a device for applying this method.

2. Description of the Prior Art

It is known to use, notably for the sterilization of food products, closed or open enclosures, in particular autoclaves, which permit high pressures and temperatures, higher than 100° C, which utilize either a liquid fluid such as water, in which the products to be sterilized are immersed, or a gaseous fluid such as steam or a suitable steam-air or steam-gas mixture. These various methods permit the enclosure to be brought to a temperature and to a pressure, more or less considerable, independant of one another.

In the autoclaves in which the rise in the temperature of sterilization and the cooling are effected by using a liquid fluid such as water, for example, in which the containers whose contents must be sterilized are entirely immersed, the rise in temperature is produced by direct or indirect heating (for example by heating by the direct injection of steam into the water, by heating by indirect action, by means of coils for example, in which a fluid circulates, by electrical resistance heating, etc.). The cooling may be effected by the same means where cooling the hot water indirectly is concerned, or the more or less sudden replacement of the hot water with cold water.

If necessary, the final phase of cooling can be done by sprinkling with cold water.

The back-pressure or excess pressure necessary in certain cases is exerted by a gas injected above the level of the fluid in the enclosure, this gas being generally compressed air.

The main drawbacks of this method are the following:

(a) a very high consumption of water, (b) a fairly considerable loss of heat, difficult to recover, the water being polluted, (c) more or less heterogeneity of the temperatures inside the batch of the containers, (d) a speed of thermal exchange between the ambient fluid and the containers which is relatively low.

It has been sought to offset the latter drawbacks by stirring the water around the containers, which permits acceleration of the heat exchanges and improvement of the homogeneity of the temperature inside of the batch. This agitation is effected generally by pumping, that is to say by recirculating the heating or cooling water by sucking it in at the base of the enclosure and reinjecting it thereinto at a higher level.

Autoclaves which use live steam as the heating fluid have the advantage of ensuring a better rise in temperature, that is to say more rapid, and an economy of water in the course of sterilization, this water being represented essentially by condensates produced during the sterilization and the cooling.

Such a thermal exchange has, however; the drawback of being a too slow because the steam contains all the greater quantity of air. The purging problems are hence very considerable. Certain methods tend to accelerate the heat exchange in the course of rise in temperature and in the sterilization phase, in particular by more or less intensive stirring of the air-steam mixtures by an internal recirculating system for the heating fluid through the batch of containers, by a turbine or if necessary by any other means of similar efficiency.

However, heating with steam has the following drawbacks:

(a) homogeneous temperature in the whole batch is difficult to achieve, even with vigorous stirring. This stirring leads to the creation of preferential paths in the batch of the containers, which preferential paths cause certain containers to benefit from a better heat exchange than those which are outside these preferential paths. Hence in general, steam or gas-steam mixtures act like water, as regards the homogeneity of the temperatures;

(b) the regulation of the excess pressure is difficult to accurately control because the injected gas, generally air, which is used to ensure the excess pressure, has a considerable coefficient of expansion. Now, certain packages are very sensitive to even very low variations in pressure in the course of the treatment;

(c) the passage from the sterilization phase to that of cooling poses delicate problems; in particular, if the cooling is done in air, by gradual condensation of the steam and by a suitable means, this cooling has proved to be extremely time-consuming, the thermal exchange between the air, even agitated, and the walls of the containers being very low and very slow.

Hence in general, water cooling has been substituted for air cooling, either by completely immersing the containers contained in the enclosure, which are until now in an environment of steam or of a steam-air or a steam-gas mixture, or by sprinkling the batch of containers with cold water.

This system has the drawback of being subjected to very great suddenness in pressure drop due to the sudden condensation of the steam and in spite of a considerable and simultaneous injection of gas (generally compressed air). The maintenance of the excess pressure applied at the end of the sterilization phase being indispensable in the case of packages sensitive to variation in pressure, it follows that considerable risks exist of the partial or total destruction of these packages. This drawback is generally offset by compensating methods. However the latter are still difficult to apply and of little reliability. In any case they do not give a sufficient mastery of the variations in pressure on the passage from the sterilization phase to the cooling phase;

(d) finally, cooling by uncontrolled sprinkling involves a fairly considerable heterogeneity of the temperatures which exist in the midst of the batch of sealed containers containing the products.

Moreover, whatever the autoclave system concerned, the consumption of energy, either electrical, (circulation or stirring), or thermal (in particular in autoclaves using a liquid fluid such as water), or in the form of a supplementary gas to maintain a pressure (such as compressed air, nitrogen, etc..) is considerable.

SUMMARY OF THE INVENTION

It is consequently intended by the present invention to provide methods and apparatus for the heat treatment of products contained in sealed containers i.e. sealed packages, which methods and apparatus respond better to the requirements of practice than previously known methods and equipment designed for the same purposes, because they overcome the drawbacks of the latter.

It is one object of the present invention to provide a method for the heat treatment of products contained in sealed containers, by heat exchange between a fluid and the packages, which method is characterized in that the heat exchange is effected by homogeneous streaming, at all points of the batch of the packages, along the walls of each of the packages, of a same liquid in the course of successive phases of the heat exchange cycle, that is to say successively in the course of the rise in temperature, in the course of the sterilization phase and in the course of the cooling phase, the temperature of said liquid being modified successively as a function of the sequence of the heat treatment phases, and the pressure or vacuum being if necessary produced inside the enclosure independently of the temperature.

In an advantageous embodiment of the method according to the present invention, the speed of rise in temperature and the speed of drop in temperature are made adjustable and controllable by actuation of suitable known devices.

In another advantageous embodiment of the method according to the present invention, the flow of the liquid heat exchange fluids takes place in circuits which are independant of the liquid and possibly gaseous phases contained in the heat treatment enclosure.

In another advantageous embodiment of the method according to the present invention, the liquid streaming heat exchange fluid is brought, by means of suitable circulating means, immediately close to the walls of each of the containers or sealed packages containing the products to be treated, with which the fluid is placed in direct contact by streaming, and to which it applies its calories or frigories with the minimum of losses.

The method according to the present invention is applied just as well to the treatment of a batch of stationary containers arranged in fixed positions, in an open or sealed enclosure (the method being then discontinuous), as to the treatment of a group of packages in motion (having a rotary movement, for example) which move regularly and continuously through one or several enclosures, each of these enclosures being able to be at atmospheric pressure or increased pressure (continuous conveyor system in one enclosure or a succession of enclosures).

The method according to the present invention has numerous applications, and is applied, notably, to sterilization, to pasteurization and to cooling of food or pharmaceutical products, packaged in sealed containers.

It is also an object of the present invention to provide an apparatus for the heat treatment of products contained in sealed containers, for the application of the above-described method, which apparatus is characterized by the combination of a liquid heat exchange fluid distribution device, respectively:

with a treatment enclosure if necessary equipped with a local repartition device for said fluid by streaming into the batch of packages to be treated in said enclosure, recirculating means for the streaming fluid into the distributing device and temperature variation means for said streaming fluid before its introduction into the distributing device, said apparatus being if necessary equipped with pressurizing means.

According to the invention, in the case where the apparatus includes a device for the local repartition of the streaming heat exchange fluid through the batch of packages to be treated, this repartition device comprises essentially divider plates or the like, substantially horizontal, superposed in the treatment enclosure, supporting superposed layers of packages to be treated, which plates comprise a plurality of perforations through which the heat exchange liquid streams in fractionated manner by repartition over all the walls of each of the packages to be treated.

According to an advantageous embodiment of the device for the homogeneous repartition of the streaming fluid according to the present invention, the perforations with which each of the divider plates are provided, are distributed regularly over the whole or over portions of each divider plate concerned.

According to a preferred modification of this embodiment, the perforations are formed on the lower surface of the divider plate and if necessary on the upper surface of the latter.

According to yet another advantageous embodiment of the apparatus according to the present invention, the distributing device for the streaming fluid through the divider plates, is constituted by a hollow sleeve, or the like, bound with a divider plate, to which it leads the streaming fluid, which sleeve is engaged in corresponding sleeves of the upper and lower divider plates to form with them, a pipe system, of constant or varying diameter, for the distribution of the streaming fluid, connected to a source of heat exchange fluid.

According to the invention, each interposed or divider plate may include one or several hollow fluid supply sleeves, and in particular, a single central sleeve may be provided connected with each of the divider plates or again, each of the divider plates may be equipped with a hollow sleeve at each of its corners.

According to another advantageous embodiment of the apparatus according to the present invention, the streaming fluid distributing device comprises a distributing system such as pipe systems provided with trickling holes through which the liquid streams, or a distributing box equipped with one or several superposed perforated plates adapted to guide the streaming of the heat exchange fluid, which distributing system is mounted at the upper part of the autoclave and is combined with a piping system for supplying the treatment enclosure with heat exchange fluid.

According to another advantageous embodiment of the invention, the distributing system is equipped with pressurizing means independent of the pressurizing means with which the treatment enclosure for the containers to be treated is possibly equipped.

According to the present invention, the divider plates can be folded back; it is moreover, advantageous to make them adjustable in height.

The apparatus according to the present invention is, in addition, advantageously equipped with a variator for the flow rate of the recirculating liquid.

The apparatus according to the present invention is also advantageously equipped with at least one direct additional inlet or liquid or gaseous heat exchange fluid either into the enclosure or into the recirculating pipe systems; it can in addition include a drain — manual or automatic — for the volume of water contained at the base of the enclosure.

Apart from the foregoing features, the invention comprises other features which will emerge from the following description.

The invention relates more particularly to the methods and apparatuses for the heat treatment of products contained in sealed containers, according to the foregoing features, as well as to the means themselves for the application of these methods and for the construction of these apparatuses, as well as the manufacturing lines or similar plants in which the methods and apparatuses according to the present invention are included.

BRIEF DESCRIPTION OF THE DRAWINGS

The invention will be better understood by means of the additional description which follows, with reference to the accompanying drawings, in which:

FIGS. 4 and 5 show diagramatically another embodiment according to the invention, of a streaming fluid distributing device, also seen in vertical axial cross section;

FIG. 6 is a plan view of the embodiment of the distributing device shown in FIG. 4;

FIG. 7 is a vertical axial diagramatic view similar to that of FIG. 1, comprising a plurality of positioning means for the containers to be treated mounted in a treatment enclosure and equipped with streaming fluid distributing devices;

It must be understood, however, that these drawings and the corresponding descriptions are given solely by way of illustration of specific embodiments according to the invention, which are not to be considered in any way limiting.

DESCRIPTION OF THE PREFERRED EMBODIMENTS

Figure 1:
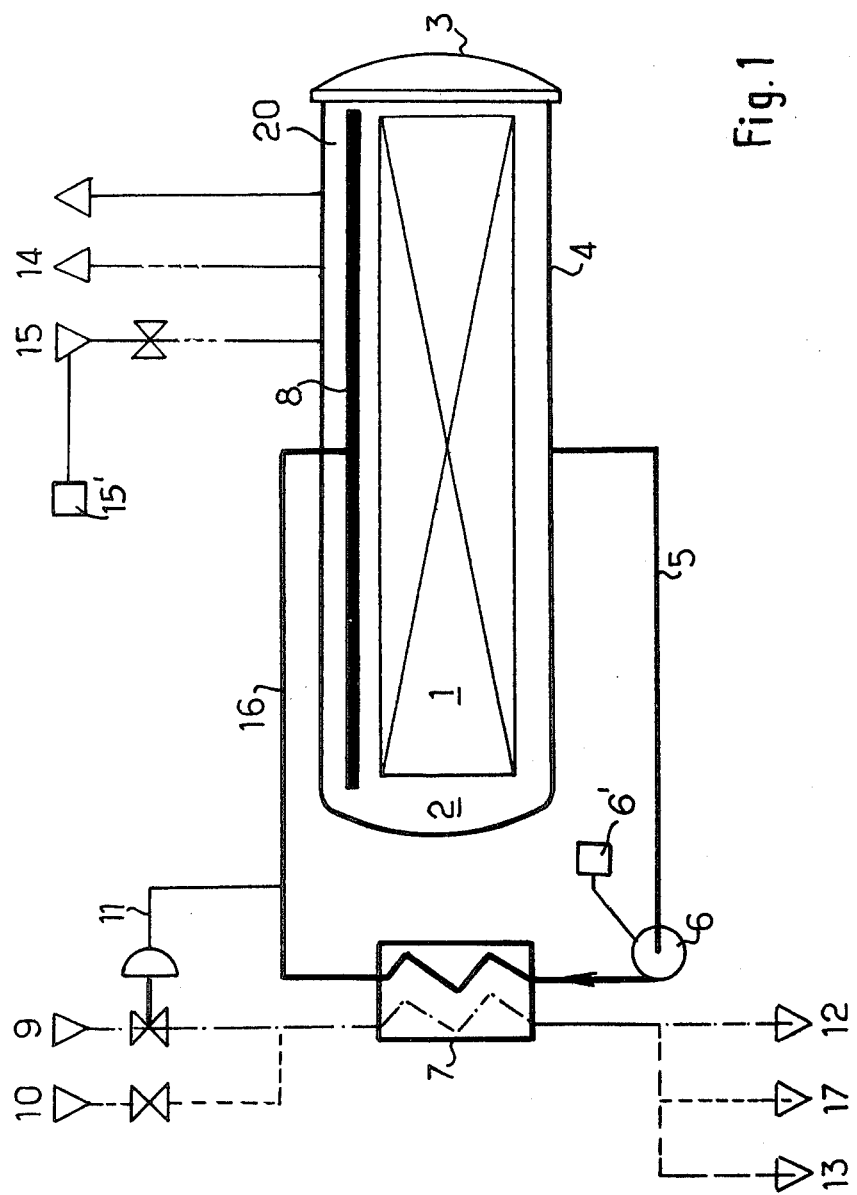
FIG. 1 shows a diagramatic view in vertical axial cross section of one embodiment of an apparatus according to the invention, which illustrates the recirculating circuit for the heat exchange fluid.

The embodiment shown in FIG. 1 of the heat treatment apparatus according to the invention for sealed packages, i.e. products contained in sealed containers, comprises an enclosure 2 equipped with a door 3 which ensures the closing of the enclosure and its fluid tightness in the case where the latter is subjected internally to the effect of the pressure or of a vacuum. Sealed packages are placed in the enclosure 2 to undergo there a suitable heat treatment such as sterilization, pasteurization, cooling, etc.

The base 4 of the enclosure 2 contains a certain amount of liquid, such as water, for example, whose level is strictly determined by the exact volume necessary to effect optimum heat exchange, to which is added the volume of the liquid serving for the heat exchange with the walls of the packages. This liquid phase which arrives by gravity at the base of the enclosure, such as an autoclave, for example, is collected by a pipe 5 connected to a pump 6 for sending the liquid into the upper part of the apparatus, after having passed through a heat exchanger 7, in which the liquid receives calories in the phase of rise in temperature or during the regulation of temperature in the sterilization phase, or frigories in the cooling phase. The piping 16 coming from the exchanger 7 terminates at the upper part of the autoclave, or the like, into which it extends through one or several holes to terminate at a distribution system 8 situated above containers 1 to be treated and covering the whole surface to be occupied by the latter. This distributing system 8 may either distribute the liquid fluid by simple gravity, or be under pressure with respect to the controlled pressure which exists in the enclosure 2. The liquid then traverses the batch of containers 1 by trickling, the heat exchange taking place either in the direction fluid → containers, in the case of heating and sterilization of the containers 1, or in the direction containers → fluid, in the case of cooling of these containers. The liquid is finally recovered at the base 4 of the autoclave 2, and can then effect a further cycle.

The heat exchanger 7 may be situated either outside the apparatus, or in suitable form, inside the enclosure 2. It plays two roles:

The exchanger is supplied, during the heating phase and the sterilization phase, with steam or any other heating fluid 9 and during the cooling phase by cold water, or any other cooling fluid 10. The supply of the heating or cooling fluid can be adjusted according to the temperature to which it is designed to bring the heat exchange fluid, by means of a suitable regulating device 11. In the heating phase and in the sterilization phase, if the heating fluid is steam, condensates will be removed through an automatic purger 12. Where a liquid heating fluid is concerned, this heat-exhausted fluid is removed through piping 17. In the cooling phase, the cooling fluid having regained calories in the exchanger 7 is removed by a piping 13.

To place the inside of enclosure 2 under pressure or excess pressure, proceedure is as follows: on the fluid-tight closing of the enclosure 2, the latter only contains a small volume of liquid and contains a large amount of air at ambient temperature and humidity. On the rise in temperature of the water recirculated to the inside of the enclosure and of the group of containers, the air heats up and expands. The pressure being regulated at any moment by an automatic device, this expanded air escapes through a purging valve 14 in order to keep the pressure inside the enclosure at the desired level; if this pressure is insufficient (in particular, if it is necessary to have a high pressure from the start of the operation), an additional volume of gas, such as air, nitrogen, or any other gas, is admitted through a valve 15 having an automatic control 15'. This same valve 15 automatically controlled, will serve, on the other hand, to admit gas to obtain the desired pressure, at other times:

(a) in the course of sterilization, when steady state conditions have been reached, it may be necessary to admit a small volume of gas to regulate the pressure inside the enclosure;

(b) when it is desired, for any reason, to increase at a given moment, the pressure inside the enclosure;

(c) on the more or less rapid cooling, which has the effect of condensing the vapor phase created on heating, in the enclosure. (This condensation enables the initial volume of water at the end of the cycle to be found again).

The apparatus shown in FIG. 1 can be completed by supplementary devices, such as:

one or several direct inlets for water actuated by manual or automatic valves, either at the base of the enclosure, or at any other spot of the enclosure or of the recirculating ducts;

manual or automatic draining of the volume of water contained at the base of the enclosure;

one or several direct injection ducts for heating fluid through manual or automatic valves, either at one or several points of the recirculating ducts;

a variator, such as a speed variator 6' for the pump 6 for the flow rate of the recirculating liquid.

Figure 3:
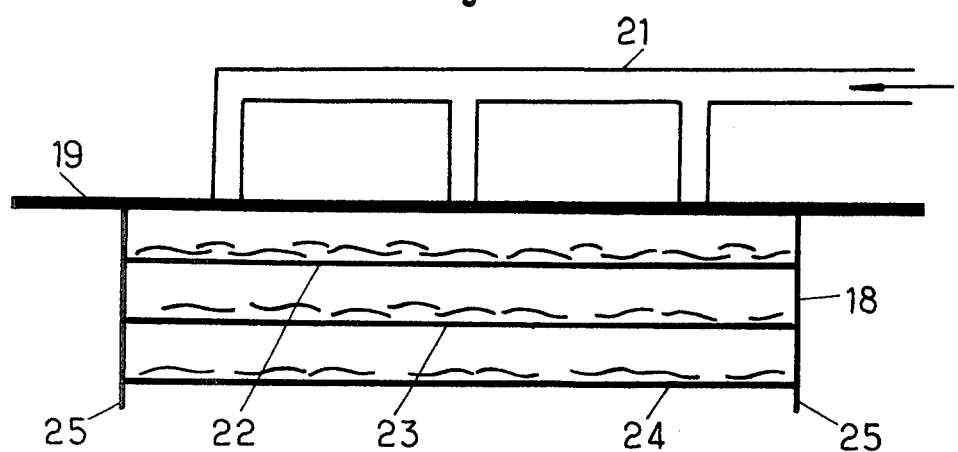
FIG. 3 shows an embodiment of the distribution system for the streaming fluid intended to stream into the treatment enclosure.
Figure 8:
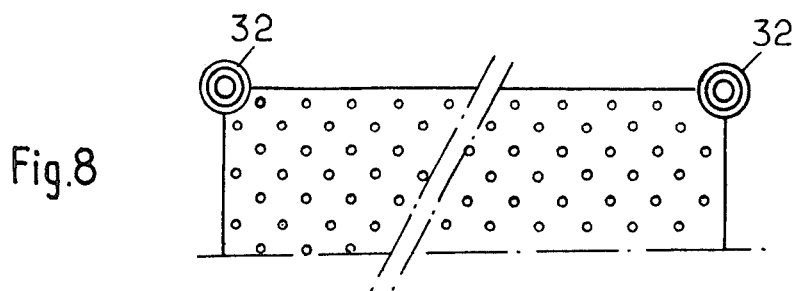
FIGS. 8 to 12 show diagramatically different embodiments of perforated divider plates for the repartition by streaming of a heat exchange fluid, equipped with fluid distributing sleeves, according to the embodiments of FIGS. 4 to 7.

The distributing system 8 of the heat exchange liquid in the apparatus is advantageously constituted by a distribution system of the type shown in FIG. 3 or by a distributing system of the type shown in FIGS. 4 to 7.

The distributing system shown in FIG. 3 includes a distributing container 18, fixed in sealed manner or not, to the upper wall 19 of the autoclave 20, above the enclosure 2. The heating or cooling fluid is apportioned to this distributing container 18 by pipes (internal or external) 21. The fluid is received, then distributed through a first plate 22 including perforations, which allow the liquid to escape under pressure or by gravity onto a second perforated plate 23 which itself distributes the liquid onto a last perforated plate 24; these three plates include regular or irregular perforations of variable sizes, but selected in suitable manner for ensuring an extremely regular distribution of the fluid, heating for example, over the first layer of containers 1, that is to say the highest layer.

The distribution container 18 can include rims 25 over its whole periphery in order to avoid useless losses by spraying fluid outside of the batch of containers. The area of the distribution container 18 covers the area of the batch of containers 1 so that the whole of the latter receives an equal amount of heating or cooling fluid. The number of perforated plates, such as 22, 23, 24 included in the distribution container 18, may be variable as a function of various parameters, and notably that of the flow rate.

Figure 2:
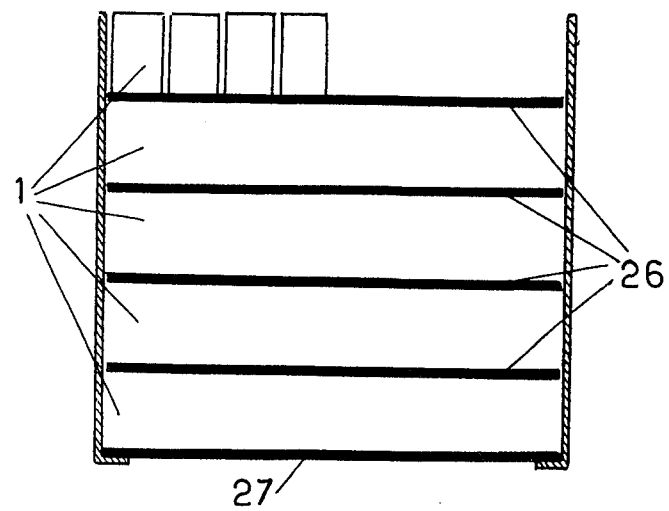
FIG. 2 shows diagramatically, in vertical axial cross section, a particular embodiment of the positioning of containers to be treated, in a heat treatment enclosure equipped with means for the local repartition by streaming, according to the invention, of the heat exchange fluid.

The containers 1 are placed in the enclosure 2 (cf. FIG. 1), if necessary in one or several baskets, in layers arranged over perforated divider plates 26 (cf. FIG. 2). The superposed layers of containers 1 receive, over their entire surface, the streaming liquid coming from a distribution system such as, for example, that which has just been described in connection with FIG. 3, or that which is shown in FIG. 4 and which will be described in more detail below. The positioning means for the containers to be treated, in the enclosure 2 (FIG. 1) include a removable or fixed bottom, constituted by a perforated plate 27 through which the liquid escapes after its passage through the batch of containers 1, by successive streamings, to reach the base 4 of the autoclave 20; this perforated plate 27 may be identical with the perforated plates 26, or different from them.

The sealed containers 1 are distributed regularly or irregularly over the perforated divider plates 26, their mode of distribution being, whatever the circumstances, such that it facilitates their positioning or their removal, as well as the regular dispersing of the streaming fluid over the divider plates 26 which divide the batch of containers 1 into horizontal layers that the liquid will successively traverse.

The perforations included in the divider plates have sizes and a distribution calculated in such a way as to permit the plates 26 to fulfill efficiently their role of regulating the fluid distribution, it being well understood that the shape, sizes, pattern and density of distribution of the perforations may vary as a function of the containers to be treated.

The perforated plates 26 are removable and replaceable in accordance with the needs. They may be folded back and adjustable in height, by utilizing suitable means.

According to the invention, the divider plates may be replaced by equivalent means, which must be considered as coming within the scope of the definition "divider plates and the like," and which can be constituted by perforated vessels called "containers" each containing one or several sealed containers to be treated.

The heating or cooling liquid coming from the distribution system (denoted generally by the reference 8) streams over the walls of each of the containers 1 of the upper layer and arrives by trickling through the perforations of the upper perforated divider plate 26, on the layer of containers 1 situated immediately below, and so on until the last layer of containers 1, the presence of the perforated divider plates 26 assuring a regular repartition of the streaming fluid without preferential paths appearing in the batch of containers 1.

Figure 9:
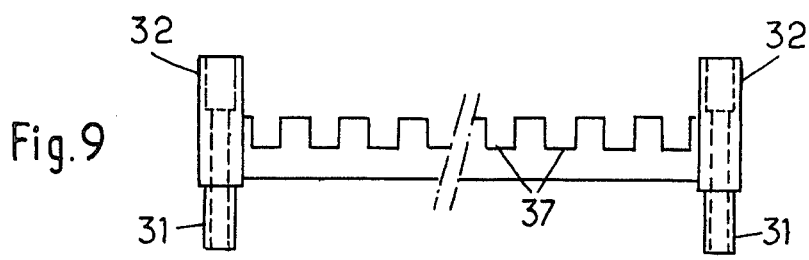
Figure 12:
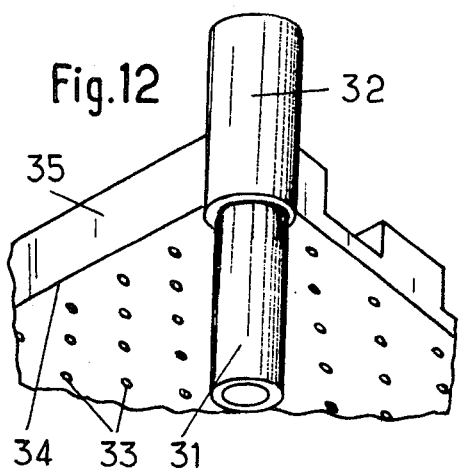

The distribution system shown in FIG. 4 comprises pipes 28 connected advantageously at their upper part to a source to fluid through a duct 29. At their base, these pipes 28 are connected together by a plate 30, advantageously perforated, which bestows its rigidity on the distribution system 28 and which contributes to ensure the streaming of the heat exchange liquid; the pipes 28 are extended, at their lower end, by a sleeve 31 which becomes inserted in a corresponding sleeve 32 oriented in the upper direction, borne by the first perforated divider plate 26. The succession of sleeves 31 which fit in sleeves 32, laterally with respect to the perforated divider plates 26, form a piping system for leading the liquid inside these divider plates which then form an internal regular network inside which the pressurized fluid flows which escapes through perforations 33 judiciously dimensioned and distributed over the lower surface 34 of the perforated divider plate 35 (cf. FIG. 12), to trickle along the walls of the sealed packages 1 of the layer situated immediately below the said plate 35. The divider plates may have perforations, not only over their lower surface, but also over their upper surface: cf. FIG. 9, so that the lower and upper bases of the sealed packages 1 of the layers situated immediately below and above, receive the heat exchange fluid by spraying through the perforations 33 and 36.

Figure 10:
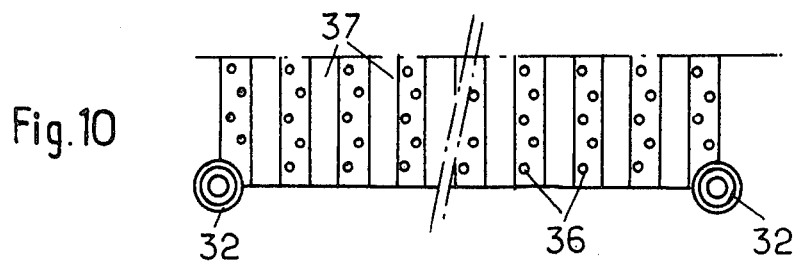
Figure 11:
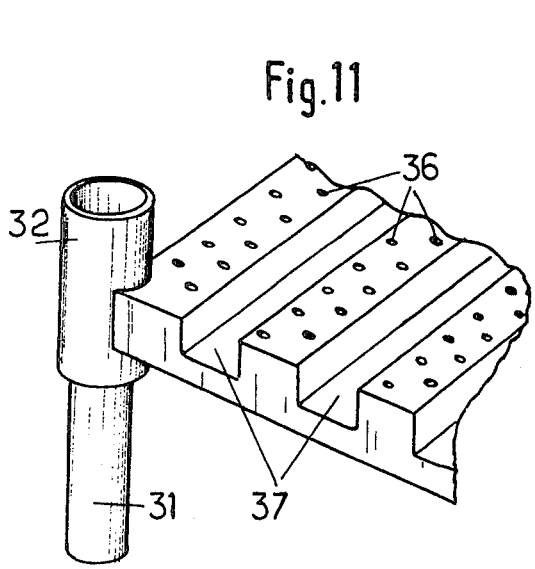

When perforations 33 and 36 are provided on the two surfaces of the divider plate, they produce a sprinkling upwards and a streaming downwards. The sprinkling liquid and the streaming liquid are removed naturally by gravity, after running over the walls of the sealed packages 1 to be treated, for example through channels 37 formed in the divider plates, according to the embodiment shown by way of non-limiting example, notably in FIGS. 9 to 11.

The divider plates shown in FIGS. 8 to 12, in the same way as the apparatuses shown in FIGS. 5 and 7 each include four hollow fluid supply sleeves, but it is self-evident that they could include a different number of them, the form of which could be different from a piping system; thus, for example, a single central sleeve could be provided in connection with each of the divider plates. Such a system is included in the general distribution of the autoclave, that is to say in the recovery and recirculation system for the heat exchange fluid, the liquid collected at the base 38 of the apparatus 39 being received in a collector 40 (cf. FIG. 7) to be sucked through a pump 41 which conducts it through a network of pipes 42 to the fluid distribution system 29-28 into the bodies of the perforated divider plates 26, through the piping formed by the sleeves 32.

The assembly formed by the combination of a streaming fluid distribution system with means for the dispersing of said fluid by streaming according to the present invention, may be arranged in a fixed or movable apparatus or may be mounted in series with other identical assemblies or the like.

The dispersing means for the heat exchange fluid essentially comprising, according to the invention, perforated divider plates, ensure a regular optimal distribution, by streaming, of the fluid over the containers to be treated, and, in certain embodiments, distribute in addition, at least partially, the heating or cooling fluid up to the level itself of the walls of each of the containers, thus ensuring a yet more intimate contact, by streaming, of the heat exchange fluid, with the containers to be treated.

It is apparent from the foregoing description that, whatever the types of application and embodiments adopted, methods and apparatuses for the heat treatment of products contained in sealed containers are obtained, which have, with respect to previously known methods and apparatuses for the same purpose, considerable advantages, in particular: Methods and apparatuses according to the present invention ensure complete homogeneity of the temperature of the fluid at all points of the treatment enclosure, that is to say at the level of each point of the surface of each container containing the product to be treated. They allow the rise in temperature of the treatment enclosure effected by means of the heat exchange liquid fluid to be of the shortest possible duration. They only use during the whole treatment cycle a single heat exchange means, constituted by the streaming of a liquid fluid along the walls of each of the containers to be treated, thus avoid sudden passages from a gaseous phase to a liquid phase and reversely, which are the source of deterioration of the containers to be treated. They permit the realization of considerable economies in energy and water, due to the recirculating system adopted according to the features of the present invention. They permit the problem of pollution of the contents of the containers which generally appears in the cooling phase, to be eliminated, the absorption of cooling water by microleaks in the containers thus not being capable of having troublesome consequences since in this case, sterile water is concerned. And they also permit the elimination of the pollution of the cooling water itself.

Thus as emerges from the foregoing description, the invention is in no way limited to those of its methods of application, embodiments and types of application which have just been described in more explicit manner; it encompasses on the contrary, all modifications which can occur to the technician skilled in the art, without departing from either the scope or the spirit of the present invention.

We claim:

1. Apparatus for the heat treatment of sealed packages, comprising
    a heat treatment enclosure filled with a gaseous atmosphere, for containing the sealed packages, said enclosure containing means to support the sealed packages;
    means to supply and distribute in a divided form a small volume of a heat exchange liquid within said enclosure and over the sealed packages by streaming said liquid over the sealed packages, said distributing means comprising a plurality of substantially horizontal divider plates superposed with respect to one another in said enclosure, said divider plates having perforations formed in their lower surfaces through which the heat exchange liquid streams downwardly in a fractionated manner over the sealed packages, at least one of said divider plates comprising a hollow member having perforations in the upper and lower surfaces thereof, at least one hollow sleeve connected with said hollow member to which it conducts the streaming liquid, said sleeve being slidably engageable with sleeves corresponding to the remainder of said divider plates to form with them piping for the distribution of the streaming liquid;
    means for feeding the heat exchange liquid to the upper portion of said enclosure and thence to the uppermost of said divider plates, said feeding means comprising means to ensure that said uppermost divider plate supports a constant charge of liquid equal at all points;
    means for recirculating the heat exchange liquid from the bottom to the top of said enclosure and at a rate sufficient to prevent the sealed packages from becoming immersed in the heat exchange liquid; and
    means for modifying the temperature of the heat exchange liquid before its introduction into said feeding means.

2. Apparatus for the heat treatment of sealed packages, comprising
    a heat treatment enclosure filled with a gaseous atmosphere, for containing the sealed packages, said enclosure containing means to support the sealed packages;
    means to supply and distribute in a divided form a small volume of a heat exchange liquid within said enclosure and over the sealed packages by streaming said liquid over the sealed packages, said distributing means comprising a plurality of substantially horizontal divider plates superposed with respect to one another in said enclosure, said divider plates having perforations formed in their lower surfaces through which the heat exchange liquid streams downwardly in a fractionated manner over the sealed packages and without substantial mixing with the gaseous atmosphere within said enclosure;
    means for feeding the heat exchange liquid to the upper portion of said enclosure and thence to the uppermost of said divider plates, said feeding means comprising means to ensure that said uppermost divider plate supports a constant charge of liquid equal at all points;

means for recirculating the heat exchange liquid from the bottom to the top of said enclosure and at a rate sufficient to prevent the sealed packages from becoming immersed in the heat exchange liquid;

means for modifying the temperature of the heat exchange liquid before its introduction into said feeding means;

wherein said distributing means comprises at least one hollow sleeve, connected with a said divider plate to which it conducts the streaming liquid, which sleeve is engaged in the corresponding sleeves of the lower and upper divider plates to form with them piping for the distribution of the streaming heat exchange liquid between said divider plates from where the liquid streams along the walls of the sealed packages.

3. Apparatus according to claim 2, wherein said feeding means further comprises a distributing container mounted at the upper part of said treatment enclosure and piping for the supply of the heat exchange liquid to said distributing container, said distributing container being equipped with a plurality of superposed perforated plates which effect homogeneous repartition of the heat exchange liquid within the heat treatment enclosure.

4. Apparatus according to claim 2, wherein the treatment enclosure comprises height regulating means for the positioning of said divider plates.

5. Apparatus according to claim 2, including means for varying the flow rate of the recirculating liquid.

6. Apparatus according to claim 2, including a valve with automatic control for said pressurizing means.

7. Apparatus in accordance with claim 2 further comprising means to seal said enclosure and means to pressurize said enclosure, said pressurizing means being independent of said distributing means.

8. Apparatus according to claim 2 wherein said distributing means is equipped with a first pressurizing means for regulating the pressure within said distributing means independent of the pressure within said enclosure and to allow the flow-rate of the liquid circulating inside said distributing means to be varied.

9. Apparatus according to claim 8, wherein said treatment enclosure is equipped with a second pressurizing means independent of said first pressurizing means for said distributing means of the streaming liquid, said second pressurizing means for the enclosure being adapted to independently regulate the pressure inside said enclosure.

10. Apparatus according to claim 9, wherein said second pressurizing means comprises air nozzles to control the internal pressure of said enclosure.

11. Apparatus according to claim 9, wherein said first pressurizing means for the distributing means comprises a pump and a speed variator for said pump for regulating the pressure generated by said pump, inside the distributing means.

* * * * *